United States Patent
Watanabe et al.

(10) Patent No.: US 11,231,391 B2
(45) Date of Patent: Jan. 25, 2022

(54) GAS SENSOR

(71) Applicant: NGK INSULATORS, LTD., Nagoya (JP)

(72) Inventors: Yusuke Watanabe, Nagoya (JP); Takayuki Sekiya, Nagoya (JP); Shota Kageyama, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 243 days.

(21) Appl. No.: 16/520,466

(22) Filed: Jul. 24, 2019

(65) Prior Publication Data
US 2020/0041442 A1 Feb. 6, 2020

(30) Foreign Application Priority Data

Aug. 3, 2018 (JP) .............................. JP2018-146837

(51) Int. Cl.
| | | |
|---|---|---|
| *G01N 27/407* | (2006.01) | |
| *G01N 27/417* | (2006.01) | |
| *G01N 33/00* | (2006.01) | |

(52) U.S. Cl.
CPC ....... *G01N 27/417* (2013.01); *G01N 27/4072* (2013.01); *G01N 27/4074* (2013.01); *G01N 33/0037* (2013.01); *F01N 2560/026* (2013.01)

(58) Field of Classification Search
CPC .. G01N 27/407; G01N 27/4071; G01N 27/41; G01N 33/0037; G01N 27/4072; G01N 27/409; F01N 2560/026
See application file for complete search history.

(56) References Cited

U.S. PATENT DOCUMENTS

| | | | |
|---|---|---|---|
| 5,763,763 A | 6/1998 | Kato et al. | |
| 2003/0062904 A1* | 4/2003 | Katafuchi | .......... G01N 33/0037 324/439 |
| 2011/0036715 A1* | 2/2011 | Horisaka | ............ G01N 27/4071 204/424 |
| 2016/0061771 A1* | 3/2016 | Mizutani | .............. G01N 27/419 204/406 |

FOREIGN PATENT DOCUMENTS

| | | | | |
|---|---|---|---|---|
| EP | 1669750 A1 * | 6/2006 | .......... | G01N 27/417 |
| JP | 3050781 B2 | 6/2000 | | |
| JP | 2014-190940 A | 10/2014 | | |
| JP | 2014-209128 A | 11/2014 | | |

* cited by examiner

*Primary Examiner* — Alexander S Noguerola
(74) *Attorney, Agent, or Firm* — Mattingly & Malur, PC

(57) ABSTRACT

A sensor element includes: a main pump cell constituted by an inner electrode provided to face a first inner space into which a measurement gas is introduced, an external electrode provided on an element surface, and a solid electrolyte therebetween; and a measurement pump cell constituted by a measurement electrode provided to face a second inner space communicated with the first inner space, an external electrode, and a solid electrolyte therebetween. A diffusion resistance from a gas inlet to the inner electrode is 200 to 1000 cm$^{-1}$. For the first inner space and a unit electrode part of the inner electrode, a space length is 2.5 to 10 mm, a space thickness is 50 to 300 μm, an electrode length/the space length is 0.5 to 1.0, and an electrode width/the space width is 0.5 to 1.0.

8 Claims, 3 Drawing Sheets

GAS SENSOR

CROSS-REFERENCE TO RELATED APPLICATION

The present application claims priority from Japanese application JP2018-146837, filed on Aug. 3, 2018, the contents of which is hereby incorporated by reference into this application.

BACKGROUND OF THE INVENTION

Field of the Invention

The present invention relates to a gas sensor obtaining a concentration of nitrogen oxide (NOx), and particularly to ensuring of accuracy in a high NOx concentration region.

Description of the Background Art

Already known is a limiting current type gas sensor (NOx sensor) using a sensor element which mainly has an oxygen ion conductive solid electrolyte as a constituent (for example, see Japanese Patent No. 3050781). In order to obtain the NOx concentration in such a gas sensor, a measurement gas is firstly introduced into a space provided inside the sensor element (an inner space) under a predetermined diffusion resistance, and oxygen in the measurement gas is pumped out in an electrochemical pump cell provided in two stages such as a main pump cell and an auxiliary pump cell (first and second electrochemical pump cells in Japanese Patent No. 3050781) to sufficiently lower the oxygen concentration in the measurement gas previously. Subsequently, NOx in the measurement gas is reduced or resolved in a measurement electrode functioning as a reduction catalyst (a third inner pump electrode in Japanese Patent No. 3050781), and oxygen generated by the reduction or the resolution is pumped out in an electrochemical pump cell including the measurement electrode other than the pump cell described above, called a measurement pump cell, for example (a third electrochemical pump cell in in Japanese Patent No. 3050781). The concentration of NOx is obtained by using a fact that current flowing in the measurement pump cell (NOx current) has a certain functional relationship with the concentration of NOx.

Also already known is an embodiment that in the gas sensor (NOx sensor), Pt to which Au is added (Au—Pt alloy) is used as a metal component of an inner pump electrode provided in an inner space to constitute a main pump cell, for purpose of suppressing the resolution of NOx when the main pump cell pumps oxygen out of the inner space and increasing a detection accuracy of NOx (for example, see Japanese Patent Application Laid-Open No. 2014-190940 and Japanese Patent Application Laid-Open No. 2014-209128).

In the gas sensor described above, the concentration of NOx is obtained based on an amount of oxygen generated by a reduction of NOx in the measurement gas reaching the measurement electrode due to catalytic action of the measurement electrode. At this time, oxygen in the measurement gas is pumped out by the electrochemical pump cell until the measurement gas reaches the measurement electrode, and this pumping-out of oxygen is performed so that the oxygen partial pressure (oxygen concentration) of the measurement gas is lowered enough to the extent not to resolve NOx. The reason is that if NOx is resolved before the measurement gas reaches the measurement electrode, the amount of NOx reaching the measurement electrode decreases, thus the concentration cannot be obtained accurately.

However, when the oxygen concentration of the measurement gas introduced into the inner space is high, NOx may be resolved at the time of pumping out oxygen. Obtained after an earnest review by the inventor of the present invention are findings that, due to a tendency where the oxygen concentration of the measurement gas in the inner space is higher in a portion closer to an upstream side (in a side closer to a gas inlet of the sensor element), a high pump voltage tends to be locally applied in a portion closer to an upstream side of the inner pump electrode in order to carry out to pump out oxygen from the measurement gas whose oxygen concentration is high, and NOx is also resolved in such a portion.

SUMMARY

The present invention relates to a gas sensor obtaining a concentration of nitrogen oxide (NOx), and particularly to ensuring of accuracy in a high NOx concentration region.

According to the present invention, in a limiting current type gas sensor including a sensor element formed of an oxygen ion conductive solid electrolyte, the gas sensor being capable of specifying a concentration of NOx in a measurement gas, the sensor element includes: a gas inlet into which a measurement gas is introduced from an outer space; a first inner space communicated with the gas inlet under a predetermined diffusion resistance; a second inner space communicated with the first inner space under a predetermined diffusion resistance; a main pump cell which is an electrochemical pump cell constituted by an inner pump electrode including one or two unit electrode parts and provided to face the first inner space, an external pump electrode provided on a surface of the sensor element, and the solid electrolyte located between the inner pump electrode and the external pump electrode; a measurement electrode provided to face the second inner space and covered by a porous protection film providing a predetermined diffusion resistance, the measurement electrode functioning as a reduction catalyst for NOx; an atmospheric air introduction layer into which atmospheric air is introduced from outside of the sensor element as a reference gas; a reference electrode covered with the atmospheric air introduction layer; and a measurement pump cell which is an electrochemical pump cell constituted by the measurement electrode, the external pump electrode, and the solid electrolyte located between the measurement electrode and the external pump electrode. When the inner pump electrode includes the two unit electrode parts, the two unit electrode parts are disposed to face each other. The main pump cell pumps out oxygen in the measurement gas introduced into the first inner space through an application of a predetermined main pump voltage between the inner pump electrode and the external pump electrode, so that oxygen partial pressure of the measurement gas in the first inner space is lowered. The measurement pump cell pumps out oxygen generated by a reduction of NOx in the measurement gas reaching near the measurement electrode in the measurement electrode, through an application of a predetermined pump voltage between the inner pump electrode and the external pump electrode. The gas sensor further includes: a concentration specifying element specifying a concentration of the NOx based on a magnitude of a NOx current flowing between the measurement electrode and the external pump electrode in the measurement pump cell. A diffusion resistance from the gas inlet to the first inner space is 200 $cm^{-1}$ or larger and 1000 cm$^{-1}$ or smaller. When the first inner space has a space length L1 as a size in a longitudinal direction of the sensor element, a space thickness t1 as a size in a thickness direction of the sensor element, and a space width w1 as a size in a width direction perpendicular to both of the longitudinal direction and the thickness direction, and the unit electrode part has an electrode length L2 as a size in the longitudinal direction and an electrode width w2 as a size in the width direction, the space length L1 is 2.5 mm or larger and 10 mm or smaller, the space thickness t1 is 50 μm or larger and 300 μm or smaller, a ratio of the electrode length relative to the space length is 0.5 or more and 1.0 or less, and a ratio of the electrode width relative to the space width is 0.5 or more and 1.0 or less.

Accordingly, even when a measurement gas having a high oxygen concentration is introduced into the first inner space, oxygen is pumped out from the first inner space while resolution in the first inner space NOx is suppressed in a range where ensuring of an NOx measurement accuracy is possible, thereby achieving a gas sensor in which influence of the introduction on the NOx measurement accuracy is small.

It is preferable that the space length L1 is 3.0 mm or larger and 3.5 mm or smaller, the space thickness t1 is 100 μm or larger and 200 μm or smaller, the ratio of the electrode length relative to the space length is 0.8 or more and 1.0 or less, the ratio of the electrode width relative to the space width is 0.9 or more and 1.0 or less.

In such a case, even when a measurement gas having a high oxygen concentration is introduced into the first inner space, the oxygen partial pressure in the first inner space is substantially maintained at a set value and NOx resolution does not occur in the first inner space, thereby achieving a gas sensor in which degradation of the NOx measurement accuracy hardly occurs.

Accordingly, an object of the present invention is to provide a gas sensor capable of measuring NOx accurately even when the oxygen concentration in the measurement gas is high.

These and other objects, features, aspects and advantages of the present invention will become more apparent from the following detailed description of the present invention when taken in conjunction with the accompanying drawings.

DESCRIPTION OF THE PREFERRED EMBODIMENTS

<Schematic Configuration of Gas Sensor>

Described first is a schematic configuration of a gas sensor 100 including a sensor element 101 according to the present embodiment. In the present embodiment, the gas sensor 100 is a limiting current type NOx sensor which detects NOx using the sensor element 101 to measure a concentration of NOx.

Figure 1:
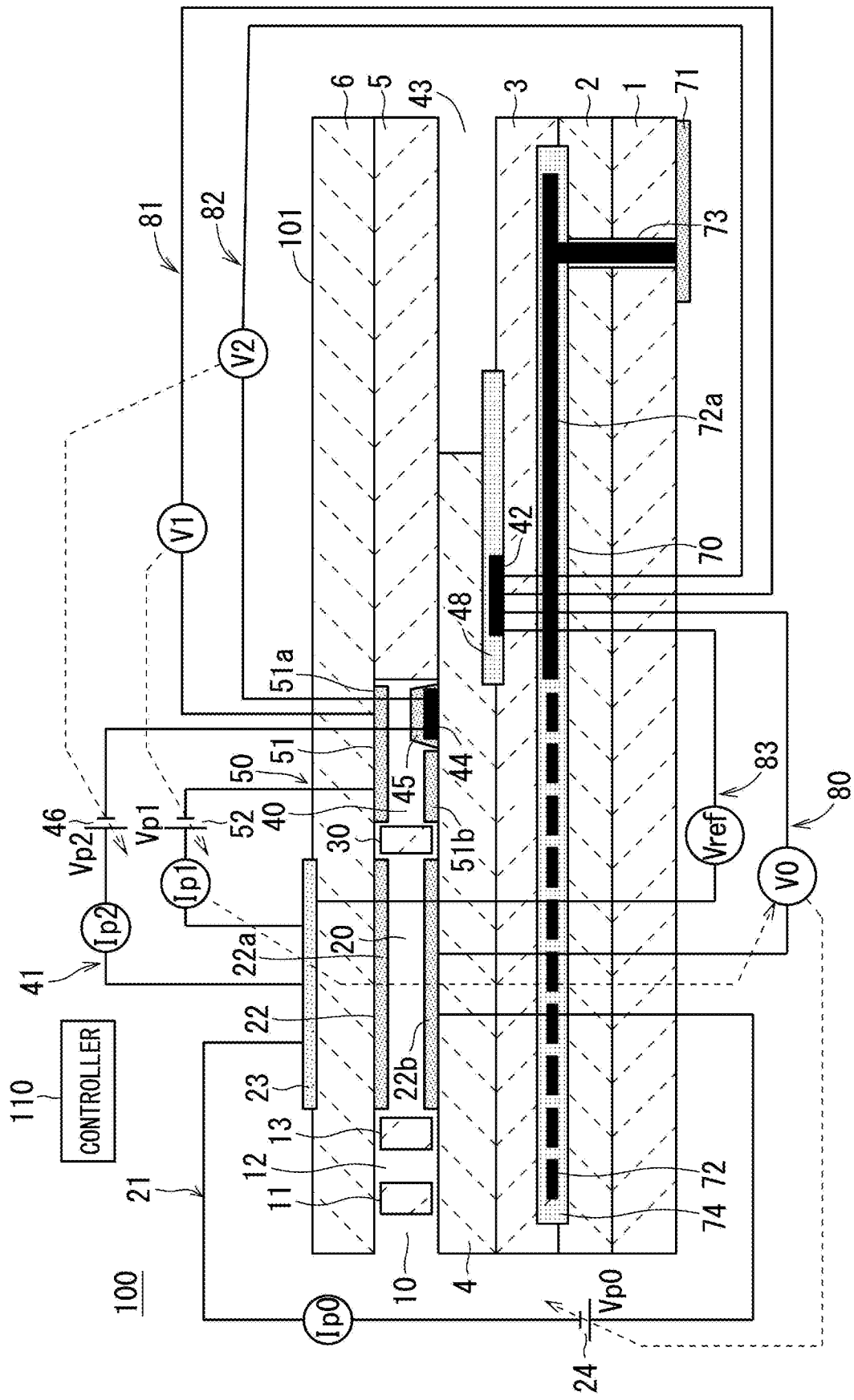
FIG. 1 is a drawing schematically showing an example of a configuration of a gas sensor 100 including a vertical sectional view of the sensor element 101 along a longitudinal direction.

FIG. 1 is a drawing schematically showing an example of a configuration of the gas sensor 100 including a vertical sectional view of the sensor element 101 along a longitudinal direction.

The sensor element 101 is a flat plate like (elongated plate like) element having a structure made up of six solid electrolyte layers of a first substrate layer 1, a second substrate layer 2, a third substrate layer 3, a first solid electrolyte layer 4, a spacer layer 5, and a second solid electrolyte layer 6, each of which is formed of zirconia (ZrO$_2$) which is an oxygen ion conductive solid electrolyte (for example, yttrium stabilized zirconia (YSZ)), laminated from a lower side in this order when seeing a drawing sheet of FIG. 1. The solid electrolyte forming these six layers is dense and airtight. In the subsequent description, a surface on an upper side of each of these six layers in FIG. 1 is simply referred to as an upper surface, and a surface on a lower side thereof is simply referred to as a lower surface in some cases. A whole part made of the solid electrolyte in the sensor element 101 is collectively referred to as a base part.

The sensor element 101 is manufactured by performing a predetermined processing and printing a circuit pattern on a ceramic green sheet corresponding to each layer, then laminating the green sheets, and further firing to integrate them with each other, for example.

A gas inlet 10, a first diffusion limiting part 11, a buffer space 12, a second diffusion limiting part 13, a first inner space 20, a third diffusion limiting part 30, and a second inner space 40 are adjacently formed to be communicated with each other in this order between a lower surface of the second solid electrolyte layer 6 and an upper surface of the first solid electrolyte layer 4 in one end of the sensor element 101.

The gas inlet 10, the buffer space 12, the first inner space 20, and the second inner space 40 are spaces in the sensor element 101 that look as if they were provided by hollowing out the spacer layer 5, an upper part thereof defined by the lower surface of the second solid electrolyte layer 6, a lower part thereof defined by the upper surface of the first solid electrolyte layer 4, and a side part thereof defined by the side surface of the spacer layer 5.

Each of the first diffusion limiting part 11, the second diffusion limiting part 13, and the third diffusion limiting part 30 is provided as two horizontally long slits (with an opening having a longitudinal direction perpendicular to the drawing sheet of FIG. 1). A region from the gas inlet 10 to the second inner space 40 is also referred to as a gas distribution part.

A reference gas introduction space 43 is provided in a position farther away from an end side in relation to the gas introduction part between the upper surface of the third substrate layer 3 and the lower surface of the spacer layer 5, a side part thereof defined by a side surface of the first solid electrolyte layer 4. Atmospheric air, for example, is introduced into the reference gas introduction space 43 as a reference gas in measuring the NOx concentration.

An atmospheric air introduction layer 48 is a layer formed of porous alumina, and the reference gas is introduced into the atmospheric air introduction layer 48 through the reference gas introduction space 43. The atmospheric air introduction layer 48 is formed to cover a reference electrode 42.

The reference electrode 42 is an electrode having a configuration of being sandwiched between the upper surface of the third substrate layer 3 and the first solid electrolyte layer 4, and the atmospheric air introduction layer 48 leading to the reference gas introduction space 43 is provided around the reference electrode 42 as described above.

An oxygen concentration (oxygen partial pressure) in the first inner space 20 and the second inner space 40 can be measured using the reference electrode 42 as described hereinafter.

The gas inlet 10 is a portion having an opening to an outer space in the gas introduction part, and the measurement gas is taken into the sensor element 101 from the outer space through the gas inlet 10.

The first diffusion limiting part 11 is a portion for providing the measurement gas taken from the gas inlet 10 of the predetermined diffusion resistance.

The buffer space 12 is a space provided for leading the measurement gas, which is introduced from the first diffusion limiting part 11, to the second diffusion limiting part 13.

The second diffusion limiting part 13 is a portion for providing the measurement gas introduced from the buffer space 12 to the first inner space 20 of the predetermined diffusion resistance.

In the introduction of the measurement gas from outside the sensor element 101 into the first inner space 20, the measurement gas rapidly taken into the sensor element 101 from the gas inlet 10 in accordance with a pressure variation of the measurement gas in the outer space (a pulsation of an exhaust gas pressure in a case where the measurement gas is an exhaust gas of a vehicle) is not directly introduced into the first inner space 20, but is introduced into the first inner space 20 after a concentration variation of the measurement gas is canceled through the first diffusion limiting part 11, the buffer space 12, and the second diffusion limiting part 13. Thus, the concentration variation of the measurement gas introduced into the first inner space 20 is substantially negligible.

The sensor element 101 of the gas sensor 100 according to the present preferred embodiment is configured so that a diffusion resistance (hereinafter referred to as a pre inner-space diffusion resistance) from the gas inlet 10 to the first inner space 20 has a value in the range of 200 $cm^{-1}$ to 1000 $cm^{-1}$. This is achieved by combining the diffusion resistance of the first diffusion limiting part 11 and the diffusion resistance of the second diffusion limiting part 13 as appropriate. The area of a section of the first inner space 20 orthogonal to the longitudinal direction (hereinafter referred to as an element longitudinal direction) of the sensor element 101 is larger than the area of a section of the second diffusion limiting part 13, and thus the first inner space 20 does not act as a diffusion limiting part on a measurement gas flowing into the first inner space 20 through the second diffusion limiting part 13, and accordingly, the pre inner-space diffusion resistance is substantially equivalent to a diffusion resistance from the gas inlet 10 to an inner pump electrode 22.

The first inner space 20 is provided as a space for adjusting the oxygen partial pressure in the measurement gas introduced through the second diffusion limiting part 13. The oxygen partial pressure is adjusted by an operation of a main pump cell 21.

The main pump cell 21 is an electrochemical pump cell constituted by the inner pump electrode 22 provided on the lower surface of the second solid electrolyte layer 6 facing the first inner space 20 and on the upper surface of the first solid electrolyte layer 4 facing the surface, an external pump electrode 23 provided to be exposed to the outer space in a region corresponding to the inner pump electrode 22 on the upper surface of the second solid electrolyte layer 6 (one main surface of the sensor element 101), and the second solid electrolyte layer 6 sandwiched between the electrodes 22 and 23.

The inner pump electrode 22 is constituted by two unit electrode parts formed on the solid electrolyte layers (the second solid electrolyte layer 6 and the first solid electrolyte layer 4) on an upper side and a lower side defining the first inner space 20. Specifically, the ceiling electrode part 22a is formed on the lower surface of the second solid electrolyte layer 6 providing a ceiling surface of the first inner space 20, and a bottom electrode part 22b is formed on the upper surface of the first solid electrolyte layer 4 providing a bottom surface of the first inner space 20. The ceiling electrode part 22a and the bottom electrode part 22b are connected to each other in a narrow conduction part extending from the electrode parts and provided along a sidewall surface (inner surface) of the spacer layer 5 constituting both side wall parts of the first inner space 20 (the illustration is omitted).

The ceiling electrode part 22a and the bottom electrode part 22b are provided in rectangular shapes in plan view. However, only the ceiling electrode part 22a or only the bottom electrode part 22b may be provided.

Each of the inner pump electrode 22 and the external pump electrode 23 are formed as a porous cermet electrode. Particularly, the inner pump electrode 22 contacting the measurement gas is formed using a material whose reducing ability on an NOx component in the measurement gas is weakened. For example, the inner pump electrode 22 is formed to have a porosity ranging from 5% to 40% and a thickness ranging from 5 μm to 20 μm as a cermet electrode made of an Au—Pt alloy containing Au substantially equal to or larger than 0.6 wt % and equal to or smaller than 1.4 wt % and $ZrO_2$. A weight ratio of the Au—Pt alloy to $ZrO_2$ may be approximately Pt:$ZrO_2$=7.0:3.0 to 5.0:5.0.

In the meanwhile, the external pump electrode 23 is formed to have a rectangular shape in a plan view as a cermet electrode made of Pt or a Pt alloy and $ZrO_2$, for example.

In the main pump cell 21, a desired pump voltage Vp0 is applied between the inner pump electrode 22 and the external pump electrode 23 by a variable source 24, and a pump current Ip0 is flowed between the inner pump electrode 22 and the external pump electrode 23 in a positive direction or a negative direction, thus oxygen in the first inner space 20 can be pumped out to the outer space or oxygen in the outer space can be pumped into the first inner space 20. The pump voltage Vp0 applied between the inner pump electrode 22 and the external pump electrode 23 in the main pump cell 21 is also referred to as the main pump voltage Vp0.

The sizes of the first inner space 20 and the inner pump electrode 22 are determined so that the measurement accuracy of the NOx concentration is ensured even when a measurement gas having a high oxygen concentration is introduced into the sensor element 101. Details thereof are described hereinafter.

The inner pump electrode 22, the second solid electrolyte layer 6, the spacer layer 5, the first solid electrolyte layer 4, the third substrate layer 3, and the reference electrode 42 constitute an electrochemical sensor cell, that is to say, a main-pump-control oxygen-partial-pressure detection sensor cell 80 to detect the oxygen concentration (oxygen partial pressure) in the atmosphere in the first inner space 20.

The oxygen concentration (oxygen partial pressure) in the first inner space 20 can be figured out by measuring an electromotive force V0 in the main-pump-control oxygen-partial-pressure detection sensor cell 80.

Furthermore, a feedback control is performed on the main pump voltage Vp0 so that the electromotive force V0 is set to constant, thus the pump current Ip0 is controlled. Accordingly, the oxygen concentration in the first inner space 20 is maintained to have a predetermined constant value.

The third diffusion limiting part 30 is a portion of providing the measurement gas, whose oxygen concentration (oxygen partial pressure) is controlled by an operation of the main pump cell 21 in the first inner space 20, of a predetermined diffusion resistance, and guiding the measurement gas to the second inner space 40.

The second inner space 40 is provided as a space for performing processing according to the measurement of nitrogen oxide (NOx) in the measurement gas introduced through the third diffusion limiting part 30. The NOx concentration is measured mainly in the second inner space 40 where the oxygen concentration is adjusted by an auxiliary pump cell 50, by an operation of a measurement pump cell 41.

In the second inner space 40, the adjustment of the oxygen partial pressure of the measurement gas whose oxygen concentration (oxygen partial pressure) has been previously adjusted in the first inner space 20 and subsequently introduced through the third diffusion limiting part 30 is further performed by the auxiliary pump cell 50. Accordingly, the oxygen concentration in the second inner space 40 can be accurately maintained constant, thus the gas sensor 100 enables the highly accurate NOx concentration measurement.

The auxiliary pump cell 50 is an auxiliary electrochemical pump cell constituted by an auxiliary pump electrode 51 having a ceiling electrode part 51a provided on almost the entire lower surface of the second solid electrolyte layer 6 facing the second inner space 40, the external pump electrode 23 (not limited to the external pump electrode 23 but an appropriate electrode outside the sensor element 101 is also applicable), and the second solid electrolyte layer 6.

The auxiliary pump electrode 51 is disposed in the second inner space 40 similarly to the inner pump electrode 22 provided in the first inner space 20 described above. In other words, the ceiling electrode part 51a is formed on the second solid electrolyte layer 6 providing a ceiling surface of the second inner space 40, and a bottom electrode part 51b is formed on the first solid electrolyte layer 4 providing a bottom surface of the second inner space 40. Each of the ceiling electrode part 51a and the bottom electrode part 51b has a rectangular shape in a plan view and is connected to each other in a conduction part provided on a sidewall surface (an inner surface) of the spacer layer 5 constituting both sidewall parts of the second inner space 40 (the illustration is omitted).

In the manner similar to the inner pump electrode 22, the auxiliary pump electrode 51 is also formed using a material whose reducing ability on an NOx component in the measurement gas is weakened.

In the auxiliary pump cell 50, a desired pump voltage Vp1 is applied between the auxiliary pump electrode 51 and the external pump electrode 23, thus oxygen in the atmosphere in the second inner space 40 can be pumped out to the outer space or oxygen can be pumped from the outer space into the second inner space 40.

The auxiliary pump electrode 51, the reference electrode 42, the second solid electrolyte layer 6, the spacer layer 5, the first solid electrolyte layer 4, and the third substrate layer 3 constitute an electrochemical sensor cell, that is to say, an auxiliary-pump-control oxygen-partial-pressure detection sensor cell 81 to control the oxygen partial pressure in the atmosphere in the second inner space 40.

The auxiliary pump cell 50 performs pumping with a variable source 52 on which a voltage control is performed based on an electromotive force V1 detected in the auxiliary pump control oxygen-partial-pressure detection sensor cell 81. Accordingly, the oxygen partial pressure in the atmosphere in the second inner space 40 is controlled so that it is low enough not to substantially influence the measurement of NOx.

In accordance with this, a pump current Ip1 thereof is used for controlling the electromotive force of the main-pump-control oxygen-partial-pressure detection sensor cell 80. Specifically, the pump current Ip1 is input, as a control signal, into the main-pump-control oxygen-partial-pressure detection sensor cell 80, and, through control of the electromotive force V0 thereof, the oxygen partial pressure in the measurement gas introduced through the third diffusion limiting part 30 into the second inner space 40 is controlled to have a gradient that is always constant. In using the gas sensor 100 as an NOx sensor, the oxygen concentration in the second inner space 40 is maintained to have a constant value of approximately 0.001 ppm by the functions of the main pump cell 21 and the auxiliary pump cell 50.

The measurement pump cell 41 measures the NOx concentration in the measurement gas in the second inner space 40. The measurement pump cell 41 is an electrochemical pump cell constituted by a measurement electrode 44 provided on the upper surface of the first solid electrolyte layer 4 facing the second inner space 40 in a position separated from the third diffusion limiting part 30, the external pump electrode 23, the second solid electrolyte layer 6, the spacer layer 5, and the first solid electrolyte layer 4.

The measurement electrode 44 is a porous cermet electrode. For example, the measurement electrode 44 is formed as a cermet electrode made of Pt or an alloy of Pt and $ZrO_2$. The measurement electrode 44 also functions as an NOx reduction catalyst for reducing NOx in the atmosphere in the second inner space 40. Furthermore, the measurement electrode 44 is covered with a fourth diffusion limiting part 45.

The fourth diffusion limiting part 45 is a film formed of a porous material mainly containing alumina ($Al_2O_3$). The fourth diffusion limiting part 45 has a function of limiting an amount of NOx flowing into the measurement electrode 44, and also functions as a protection film of the measurement electrode 44.

The measurement pump cell 41 can pump out oxygen generated by the resolution of NOx in the atmosphere around the measurement electrode 44 and detect a generation amount of oxygen as a pump current Ip2.

The second solid electrolyte layer 6, the spacer layer 5, the first solid electrolyte layer 4, the third substrate layer 3, the measurement electrode 44, and the reference electrode 42 constitute an electrochemical sensor cell, that is to say, a measurement-pump-control oxygen-partial-pressure detection sensor cell 82 to detect the oxygen partial pressure around the measurement electrode 44. A variable source 46 is controlled based on an electromotive force V2 detected in the measurement-pump-control oxygen-partial-pressure detection sensor cell 82.

The measurement gas introduced into the second inner space 40 reaches the measurement electrode 44 through the fourth diffusion limiting part 45 under a condition where the oxygen partial pressure is controlled. NOx in the measurement gas around the measurement electrode 44 is reduced ($2NO \rightarrow N_2+O_2$), and oxygen is generated. The generated oxygen is pumped by the measurement pump cell 41. At this time, an electromotive force Vp2 of the variable source 46 is controlled so that a control voltage V2 detected in the measurement pump control oxygen partial pressure detection sensor cell 82 is set to constant. Since the amount of oxygen generated around the measurement electrode 44 is proportional to the NOx concentration in the measurement gas, the NOx concentration in the measurement gas is calculated using the pump current Ip2 in the measurement pump cell 41. The pump current Ip2 is also referred to as the NOx current Ip2 hereinafter.

If the measurement electrode 44, the first solid electrolyte layer 4, the third substrate layer 3, and the reference electrode 42 are combined to constitute an oxygen-partial-pressure detection means as an electrochemical sensor cell, an electromotive force in accordance with a difference of an amount of oxygen generated by the reduction of the NOx component in the atmosphere around the measurement electrode 44 and an amount of oxygen contained in a reference atmosphere can be detected, and accordingly, a concentration of the NOx component in the measurement gas can be also obtained.

The second solid electrolyte layer 6, the spacer layer 5, the first solid electrolyte layer 4, the third substrate layer 3, the external pump electrode 23, and the reference electrode 42 constitute an electrochemical sensor cell 83, and the oxygen partial pressure in the measurement gas outside the sensor can be detected by an electromotive force Vref obtained by the sensor cell 83.

The sensor element 101 further includes a heater part 70 having a function of adjusting a temperature for heating sensor element 101 and keeping the temperature, in order to increase oxygen ion conductivity of the solid electrolyte constituting the base part.

The heater part 70 mainly includes a heater electrode 71, a heater element 72, a heater lead 72a, a through hole 73, and a heater insulating layer 74. The heater part 70 is embedded in the base part of the sensor element 101 except for the heater electrode 71.

The heater electrode 71 is an electrode formed to contact the lower surface of the first substrate layer 1 (the other main surface of the sensor element 101).

The heater element 72 is a resistance heating element provided between the second substrate layer 2 and the third substrate layer 3. The heater element 72 generates the heat by supplying power from the outside of the sensor element 101 via the heater electrode 71, the through hole 73, and the heater lead 72a which function as an energizing path. The heater element 72 is formed of Pt or mainly of Pt. The heater element 72 is embedded in a predetermined region in the sensor element 101 on a side including the gas introduction part so as to oppose the gas introduction part in a thickness direction of the element. The heater element 72 is provided to have a thickness of approximately 10 μm to 20 μm.

In the sensor element 101, the current is flowed into the heater element 72 via the heater electrode 71, thereby making the heater element 72 generate the heat, thus each part of the sensor element 101 can be heated to a predetermined temperature and kept to have the temperature. Specifically, the sensor element 101 is heated so that the temperature of the solid electrolyte and the electrode near the gas introduction part increases to approximately 700° C. to 900° C. The heating processing increases the oxygen ion conductivity of the solid electrolyte constituting the base part in the sensor element 101. The heating temperature at the time of heating by the heater element 72 in a case of using the gas sensor 100 (in a case of driving the sensor element 101) is referred to as a sensor element driving temperature.

The gas sensor 100 further includes a controller 110 controlling the operation of each part and specifying the NOx concentration based on the NOx current Ip2.

In the gas sensor 100 having such a configuration, oxygen contained in the measurement gas is pumped out through the operation of the main pump cell 21 and further of the auxiliary pump cell 50, and the measurement gas whose oxygen partial pressure is lowered enough not to substantially influence the measurement of NOx (for example, 0.0001 ppm to 1 ppm) reaches the measurement electrode 44. In the measurement electrode 44, NOx in the measurement gas which has reached the measurement electrode 44 is reduced, and oxygen is generated. The generated oxygen is pumped out by the measurement pump cell 41. The NOx current Ip2 flowing at the time of pumping out oxygen has a certain functional relationship (referred to as sensitivity characteristics hereinafter) with the concentration of NOx in the measurement gas.

The sensitivity characteristics are previously specified using a plural types of model gas whose NOx concentrations are already known in advance of the actually use of the gas sensor 100, and data thereof is stored in the controller 110. In the actual use of the gas sensor 100, signals indicating a value of the NOx current Ip2 flowing in accordance with the NOx concentration in the measurement gas is provided to the controller 110 from moment to moment, and the NOx concentration is continuously calculated based on the value and the specified sensitivity characteristics and output in the controller 110. According to the gas sensor 100, the NOx concentration in the measurement gas can be obtained almost in real time.

Although the sensitivity characteristics should in principle have a perfect proportional relation between the NOx concentration and the NOx current Ip2, the measurement gas reaching the measurement pump cell 41 contains a small amount of oxygen not pumped out in the main pump cell 21 and the auxiliary pump cell 50 when the gas sensor 100 is actually used. Thus, even when no NOx is contained in the measurement gas, the NOx current Ip2 is not completely zero. The NOx current Ip2 in this case is referred to as an offset current. Usually, in the gas sensor 100, the sensitivity characteristics are specified in consideration of the presence of such offset current, but from the viewpoint of ensuring the measurement accuracy, the offset current is preferably smaller, and it is not preferable that the offset current fluctuates.

<Reducing Influence of Introduction of Measurement Gas Having High Oxygen Concentration>

The sensor element 101 of the gas sensor 100 according to the present preferred embodiment generally has the above-described configuration, but more specifically, satisfies some configurational requirements from the viewpoint of suppressing NOx resolution in the first inner space 20 to ensure the measurement accuracy even when the measurement gas having a high oxygen concentration is continuously introduced to the inside. In the following description, the inner pump electrode 22 has both the ceiling electrode part 22a and the bottom electrode part 22b in the same shape at the same position in plan view unless otherwise stated. Since contribution from the conduction part regarding the resolution of NOx may be negligible, thus the term "inner pump electrode 22" indicates a part except for the conduction part in the following description.

First, as a premise, the sensor element 101 is configured so that the pre inner-space diffusion resistance satisfies the range of 200 $cm^{-1}$ to 1000 $cm^{-1}$ as described above to appropriately adjust the flow rate of the measurement gas introduced into the first inner space 20 from the outside.

In the case that the pre inner-space diffusion resistance is smaller than 200 $cm^{-1}$, the flow rate when the measurement gas containing oxygen is introduced into the first inner space 20 is large, and thus the absolute amount of oxygen in the first inner space 20 is large. Accordingly, the main pump voltage Vp0 and the pump current Ip0 inevitably become large because it is necessary to pump out such oxygen. In such a case, NOx contained in the measurement gas and which should normally reach the vicinity of the measurement electrode 44 in the second inner space 40 is likely to resolve in the first inner space 20 by the pumping of the main pump cell 21. In addition, if the flow rate of the measurement gas is excessively large, the measurement gas may flow out to the second inner space 40 without sufficiently pumping out oxygen. This potentially leads to increase in the offset current. Any of these leads to decrease in the detection accuracy of NOx in the gas sensor 100, and thus is not preferable.

In the case that the pre inner-space diffusion resistance is larger than 1000 cm$^{-1}$, the absolute amount of NOx reaching the vicinity of the measurement electrode 44 decreases because the flow rate of the measurement gas introduced to the first inner space 20 is small. Such a case is not preferable because NOx cannot be accurately detected or the responsivity is reduced.

When the flow rate of the measurement gas introduced into the first inner space 20 is appropriate, the quality of pumping of oxygen from the first inner space 20 depends on the balance between the size of the first inner space 20 and the capacity of the main pump cell 21. Since the capacity of the main pump cell 21 largely depends on the size of the inner pump electrode 22 provided to face the first inner space 20, the quality of pumping of oxygen from the first inner space 20 mainly depends on the size of the first inner space 20 and the ratio of this size and the size of the inner pump electrode 22.

Figure 2:
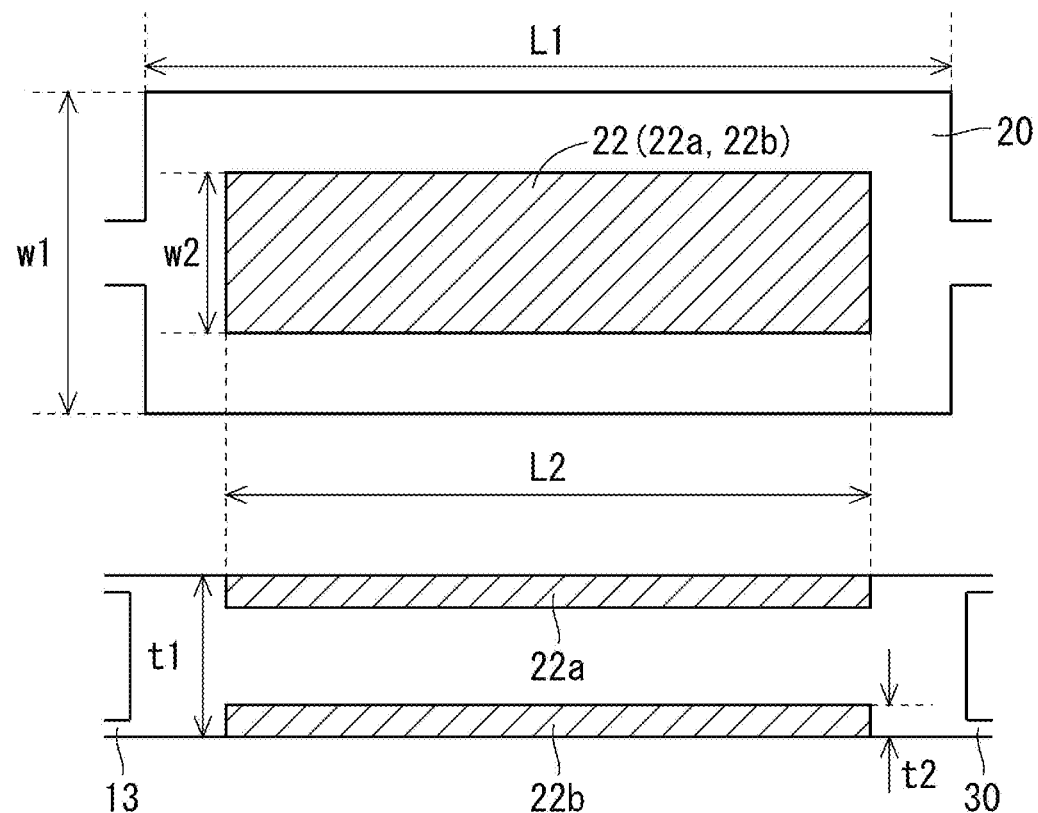
FIG. 2 is a drawing for description of sizes of a first inner space 20 and an inner pump electrode 22 provided on upper and lower surfaces of the first inner space 20.

FIG. 2 is a drawing for description of the sizes of the first inner space 20 and the inner pump electrode 22 provided on the upper and lower surfaces of the first inner space 20. In FIG. 2, the right and left direction in the drawing is the element longitudinal direction, and a dimensional drawing at a plane perpendicular to the thickness direction is shown on the upper side, and a dimensional drawing at a plane perpendicular to the width direction is shown on the lower side.

In the gas sensor 100 according to the present preferred embodiment, the sensor element 101 is configured so that the relation between these sizes are preferable. Specifically, first, as shown in FIG. 2, when the first inner space 20 has a space length L1 as a size in the element longitudinal direction, a space thickness t1 as a size in the thickness direction (stacking direction of the solid electrolyte layers) of the sensor element 101, and a space width w1 as a size in the width direction perpendicular to both of the element longitudinal direction and the thickness direction, the first inner space 20 satisfies the following requirements (a) to (b).

(a) Space length L1: 2.5 mm or larger (10 mm or smaller)
(b) Space thickness t1: 50 μm or larger and 300 μm or smaller The requirements (a) and (b) are the size requirements of the first inner space 20, which affects the flow of the measurement gas from the upstream side (specifically, the second diffusion limiting part 13) to the downstream side (specifically, the third diffusion limiting part 30).

In the case that the space length L1 is smaller than 2.5 mm, the interval between the upstream and downstream sides of the first inner space 20 is small, and thus the pumping capacity of the main pump cell 21 is not sufficient even if the inner pump electrode 22 is maximally provided.

Accordingly, when the measurement gas having a high oxygen concentration continuously flows in from the upstream side, the measurement gas accumulates in the first inner space 20 without sufficiently pumping out of oxygen upon application of the main pump voltage Vp0. More specifically, since the oxygen concentration in the first inner space 20 increases toward the upstream where the measurement gas flows in, the main pump voltage Vp0 tends to increase near the upstream side of the inner pump electrode 22, which is highly likely to cause local NOx resolution at the place.

As such accumulation progresses, outflow to the downstream side occurs through the third diffusion limiting part 30. In other words, the measurement gas flows out to the downstream side without oxygen being pumped out to a set oxygen partial pressure. This is not preferable because it leads to increase in the offset current.

As a matter of course, these tendencies are more significant as the size of the inner pump electrode 22 is smaller.

On the other hand, the case that the space length L1 is excessively large does not cause any particular problem in dealing with the situation that the measurement gas has a high oxygen concentration, but the space length L1 exceeding 10 mm means that the sensor element 101 is long and therefore disadvantageous in terms of cost and that the response time is long, and thus is not preferable.

In the case that the space thickness t1 is smaller than 50 μm, the ceiling electrode part 22a and the bottom electrode part 22b are close to each other, and a gap at a part where the measurement gas flows decreases, and thus the pumping oxygen is preferentially performed near the upstream side of the inner pump electrode 22. Notable problems are unlikely to occur at the time when the measurement gas starts to flow from the upstream side, but when the measurement gas is continuously introduced with high oxygen concentration, the oxygen concentration in the first inner space 20 progressively increases from the upstream side, and thus, nearer the upstream side, it is more likely that the main pump voltage Vp0 locally increases and NOx resolution is caused. In addition, as a result of such remarkable resolution, the measurement gas accumulates in the first inner space 20 with oxygen not sufficiently pumped out therefrom and eventually flows out from the downstream side, which potentially causes increase of the offset current. All these are not preferable. Although the inner pump electrode 22 needs to be thinner as the space thickness t1 decreases in order to ensure a gap through which the measurement gas flowing, the thinning has a limit, and thus it is not preferable to excessively reduce the space thickness t1.

In the case that the space thickness t1 exceeds 300 μm, the ceiling electrode part 22a and the bottom electrode part 22b are separated, and thus a relatively small amount of the measurement gas introduced into the first inner space 20 contacts the inner pump electrode 22. Accordingly, the oxygen pumping by the main pump cell 21 is difficult to progress, and most of the measurement gas accumulates without contacting the inner pump electrode 22 and being subjected to the oxygen pumping, and then flows out from the downstream side. As a result, the offset current is undesirably increased.

The space width w1 represents a size in a direction perpendicular to the direction from the upstream side (specifically, the second diffusion limiting part 13) to the downstream side (specifically, the third diffusion limiting part 30). Moreover, from the viewpoint of suppressing increase of the oxygen concentration of the measurement gas in the first inner space 20, it is important that the electrode is provided so as to match the value of the space width w1, as described later. It may be set in consideration of circumstances of production of the sensor element 101, the balance with other parts, the cost, and the like. For example, the range of 1.5 mm to 3.5 mm inclusive is exemplarily provided.

In addition to the above requirements (a) and (b), as shown in FIG. 2, when the sensor element 101 has an electrode length L2 as the sizes of the ceiling electrode part 22a and the bottom electrode part 22b of the inner pump electrode 22 in the element longitudinal direction, an electrode thickness t2 as a size in the thickness direction, and an electrode width w2 as a size in the width direction, the size of the first inner space 20 and the sizes of the ceiling electrode part 22a and the bottom electrode part 22b of the inner pump electrode 22 satisfy the following requirements (c) to (d).

(c) The ratio (length ratio) L2/L1 of the electrode length L2 relative to the space length L1: 0.5 or more (1.0 or less)

(d) The ratio (width ratio) w2/w1 of the electrode width w2 relative to the space width w1: 0.5 or more (1.0 or less)

The requirements (c) and (d) are related to the pumping capacity of the main pump cell 21. In the following description, the length L2, the width w2, and the thickness t2 of each of the ceiling electrode part 22a and the bottom electrode part 22b are also simply referred to as the length L2, the width w2, and the thickness t2 of each unit electrode part of the inner pump electrode 22.

In the case that the value of the length ratio L2/L1 is lower than 0.5, and, in the case that the value of the width ratio w2/w1 is lower than 0.5, the pumping capacity of the main pump cell 21 is not sufficient as compared to the size of the first inner space 20, and thus when the flowing measurement gas has a high oxygen concentration, the oxygen concentration in the first inner space 20 progressively increases from the upstream side, and nearer the upstream side, it is more likely that the main pump voltage Vp0 locally increases and NOx resolution is caused. In addition, the measurement gas flows out from the downstream side with oxygen not sufficiently pumped out therefrom, and thus the offset current is likely to increase. All these are not preferable.

It is clear from the definitions that the upper limits of the length ratio L2/L1 and the width ratio w2/w1 are both 1.0. In other words, the value of the length ratio L2/L1 is 1.0 when the inner pump electrode 22 is formed over the entire space length L1, and the value of the width ratio w2/w1 is 1.0 when the inner pump electrode 22 is formed over the entire space width w1.

In addition, the ceiling electrode part 22a and the bottom electrode part 22b of the inner pump electrode 22 are provided so that the requirements (c) and (d) are satisfied, the thickness t2 is 5 μm or larger and 30 μm or smaller, preferably 10 μm or larger and 20 μm or smaller, and the area (plane area) S2=L2w2 in plan view is 5 mm$^2$ or larger and 20 mm$^2$ or smaller.

The lower limit of the thickness t2 is 5 μm because it is difficult to control the thickness to a predetermined value less than 5 μm in forming the inner pump electrode 22.

In the case that the thickness t2 is larger than 30 μm, and, in the case that the area S2 is larger than 20 mm$^2$, the reactivity of NOx in the inner pump electrode 22 increases, and the NOx resolution is likely to occur, which is not preferable.

In the case that the area S2 is less than 5 mm$^2$, the impedance in the main pump cell 21 increases and the value of the pump current Ip0 becomes too small, or the main pump voltage Vp0 easily increases due to insufficient pumping capacity and accordingly the NOx resolution is likely to occur, which are not preferable.

The thickness t2 of each unit electrode part of the inner pump electrode 22 may be determined in accordance with the thickness t1 of the first inner space 20. Specifically, based on the requirement (b) described above, the ratio $t2_{all}/t1$ of the sum of the thickness t2 of the inner pump electrode 22 (the sum of the thicknesses of the ceiling electrode part 22a and the bottom electrode part 22b) $t2_{all}$ relative to the thickness t1 of the first inner space may be 0.06 or more and 0.60 or less.

In the gas sensor 100 according to the present preferred embodiment, when the sensor element 101 satisfies the requirements (a) to (d) described above, and thus the pumping out of oxygen from the first inner space 20 is suitably performed even when the oxygen concentration in the measurement gas is high, while the NOx resolution in the first inner space 20 is suppressed, thereby ensuring the measurement accuracy.

The disposed positions of the ceiling electrode part 22a and the bottom electrode part 22b in the first inner space 20 when the electrode length L2 and the electrode width w2 are smaller than the space length L1 and the space width w1, respectively, are not particularly limited. For example, the barycenter position of the first inner space 20 may or may not coincide with the barycenter positions of the ceiling electrode part 22a and the bottom electrode part 22b in plan view. In the latter case, the parts may be disposed on the upstream side or the downstream side in the element longitudinal direction. It is preferable that the ceiling electrode part 22a and the bottom electrode part 22b are symmetrically disposed in the element width direction, but it is not essential.

<Manufacturing Process of Sensor Element>

Described next is a process of manufacturing the sensor element 101 having the configuration and the feature described above. In the present embodiment, the sensor element 101 is manufactured by forming a laminated body formed of green sheets containing an oxygen ion conductive solid electrolyte such as zirconia as a ceramic component, and then cutting and firing the laminated body.

Figure 3:
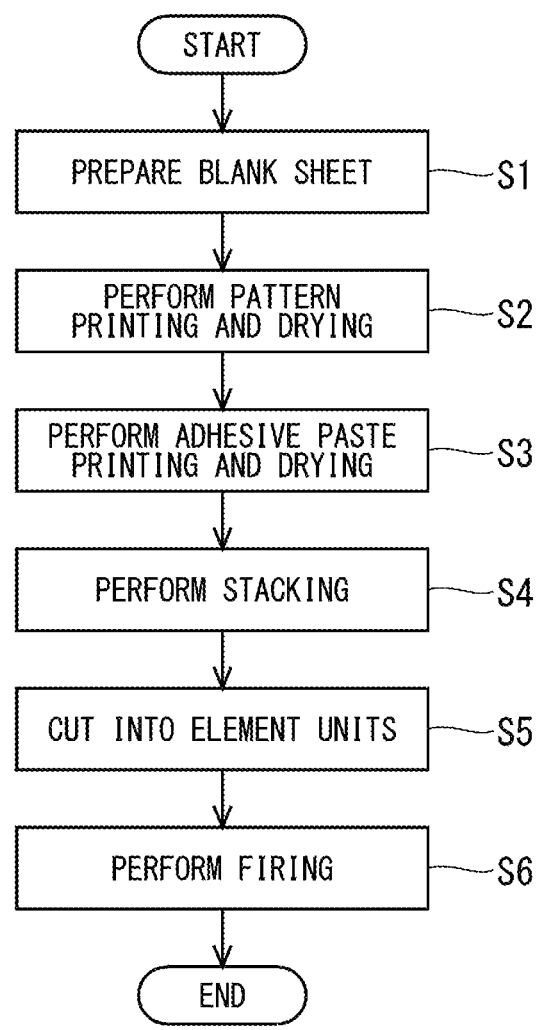
FIG. 3 is a drawing showing a flow of processing in manufacturing a sensor element 101.

Described hereinafter as an example is a case of manufacturing the sensor element 101 including the six layers illustrated in FIG. 1. Prepared in such a case are six green sheets corresponding to the first substrate layer 1, the second substrate layer 2, the third substrate layer 3, the first solid electrolyte layer 4, the spacer layer 5, and the second solid electrolyte layer 6. FIG. 3 is a drawing showing a flow of processing in manufacturing a sensor element 101.

In manufacturing the sensor element 101, firstly, a blank sheet (not shown) which is a green sheet on which no pattern is formed is prepared (Step S1). As the sensor element 101 including the six layers is manufactured, six blank sheets are prepared to correspond to each layer. In particular, for forming the spacer layer 5, a thickness of the green sheet is determined so that the requirement (b) is satisfied in the end.

The blank sheets have a plurality of sheet holes used for alignment in performing a printing and laminating the sheets. The sheet hole is previously formed in the blank sheet through, for example, punching processing using a punching device in a stage prior to the pattern formation. Green sheets corresponding to layers including the inner spaces also include penetrating portions corresponding to the inner spaces, which are also provided by the similar punching processing previously. The formation of the penetrating portion is performed in such a manner that the requirement (a) is satisfied in the sensor element 101 obtained in the end. A thickness of each blank sheet corresponding to each layer of the sensor element 101 needs not be the same as each other.

After the blank sheet corresponding to each layer is prepared, the pattern printing and dry processing are performed on each blank sheet (Step S2). Formed specifically are patterns of various types of electrodes, a pattern of the fourth diffusion limiting part 45, patterns of the heater element 72 and the heater insulating layer 74, and a pattern of an inner wiring not shown in the drawings. An application or a placement of a sublimation material for forming the first diffusion limiting part 11, the second diffusion limiting part 13, and the third diffusion limiting part 30 is also performed at a timing of the pattern printing. The application or disposition is performed in such a manner that the pre inner-space diffusion resistance satisfies the range of 200 $cm^{-1}$ to 1000 $cm^{-1}$ as described above in the sensor element 101 obtained in the end.

The printing of each pattern is performed by applying a pattern formation paste prepared in accordance with characteristics required for each formation object on the blank sheet using a known screen printing technique. A known drying means can be used for drying processing after the printing.

In particular, the paste forming the inner pump electrode 22 is prepared and applied so that the inner pump electrode 22 obtained in the end satisfies at least the requirements (c) to (d).

After the pattern printing on each blank sheet is finished, processing of printing and drying an adhesive paste for laminating and attaching the green sheet corresponding to each layer on and to one another is performed (Step S3). A known screen printing technique can be used for printing the adhesive paste, and a known drying means can be used for drying processing after the printing.

Subsequently, the green sheets on which an adhesive agent has been applied are stacked in a predetermined order, and the stacked green sheets are crimped under a predetermined temperature condition and pressure condition to form one laminated body (Step S4). Specifically, the crimping is performed by stacking and holding the green sheets to be laminated on a predetermined laminating jig not shown while aligning the green sheets using the sheet holes, and then heating and pressurizing the green sheets together with the laminating jig using a laminating machine such as a known oil hydraulic pressing machine. The pressure, the temperature, and the time for heating and pressurizing depend on the laminating machine to be used, however, an appropriate condition may be determined to be able to achieve a favorable lamination.

When the laminated body is obtained as described above, subsequently, the laminated body is cut out at a plurality of locations to obtain an individual unit (referred to as the element body) of the sensor element 101 (Step S5).

The firing is performed on the element body at a firing temperature of approximately 1300° C. to 1500° C. (Step S6). The sensor element 101 is thereby manufactured. In other words, the sensor element 101 is manufactured through integrally firing the solid electrolyte layer and the electrode. The firing temperature is preferably set to 1200° C. to 1500° C. (for example, 1400° C.). The integrated firing is performed in the above manner, thus each electrode has sufficient adhesion strength in the sensor element 101.

The sensor element 101 obtained in such a manner is stored in a predetermined housing, and incorporated into a main body (not shown) of the gas sensor 100.

<Modifications>

As described above, only one of the ceiling electrode part 22a and the bottom electrode part 22b may be provided as the inner pump electrode 22, but in such a case, the thickness t2 may be 5 μm or larger and 30 μm or smaller as in the case in which both electrode parts are provided. However, the thickness ratio $t2_{all}/t1$ needs to satisfy the range of 0.06 to 0.60 inclusive with only one of the unit electrode parts as in the case in which both electrode parts are provided. Accordingly, the ratio $t2_{all}/t1$ of the sum of the thickness of the inner pump electrode 22 relative to the space thickness needs to satisfy the range of 0.06 to 0.60 inclusive also in the case in which the ceiling electrode part 22a and the bottom electrode part 22b are both provided.

As for the range of the area S2, in view of the case in which both electrode parts are provided, the upper limit may be 20 $mm^2$ as in the case in which both electrode parts are provided, but the lower limit thereof should be 10 $mm^2$, which is the sum of lower limits in the case in which both electrode parts are provided, in the relation with the impedance in the main pump cell 21.

The thickness t2 and the area S2 do not need to be identical between the ceiling electrode part 22a and the bottom electrode part 22b.

EXAMPLE (Manufacturing of Gas Sensor)

A total of 16 types of gas sensors 100 (No. 1 to No. 16) having mutually different combinations of the pre inner-space diffusion resistance, the space length L1 and the space thickness t1 of the first inner space 20, and the length ratio L2/L1 and the width ratio w2/w1 of the first inner space 20 and the inner pump electrode 22 were manufactured.

Specifically, the pre inner-space diffusion resistance, the space length L1, the space thickness t1, the length ratio L2/L1, and the width ratio w2/w1 were different as follows.

The pre inner-space diffusion resistance: nine levels of 150 $cm^{-1}$, 200 $cm^{-1}$, 300 $cm^{-1}$, 400 $cm^{-1}$, 500 $cm^{-1}$, 600 $cm^{-1}$, 700 $cm^{-1}$, 800 $cm^{-1}$, and 1000 $cm^{-1}$; The space length L1: six levels of 2.0 mm, 2.5 mm, 3.0 mm, 3.5 mm, 7.0 mm, and 8.0 mm;

The space thickness t1: nine levels of 40 μm, 50 μm, 80 μm, 100 μm, 120 μm, 150 μm, 200 μm, 300 μm, and 350 μm;

The length ratio L2/L1: seven levels of 0.4, 0.5, 0.6, 0.7, 0.8, 0.9, and 1.0; and The width ratio W2/w1: eight levels of 0.40, 0.50, 0.60, 0.75, 0.80, 0.85, 0.90, and 0.95.

The gas sensors of No. 1 to No. 10 satisfy all requirements (a) to (d), and the gas sensors of No. 11 to No. 16 do not satisfy at least one of the requirements (a) to (d).

The space width w1 was in the range of 1.5 mm to 3.5 mm. The electrode thickness sum $t2_{all}$ was changed in the range of 10 μm to 60 μm so that the ratio $t2_{all}/t1$ is in the range of 0.06 to 0.60.

The formation modes of components other than the above were same in all gas sensors 100.

(Determination 1)

Measurement using a test gas having an oxygen concentration of 18% and the balance of $N_2$ as a measurement gas was performed with each gas sensor 100 manufactured as described above, the value of the offset current was calculated, and the quality of pumping out from the first inner space 20 by the main pump cell 21 was determined from the magnitude of the value. The sensor element drive temperature was 830° C.

The offset current is the pump current (NOx current) Ip2 flowing through the measurement pump cell 41 when NOx is not contained in the measurement gas, and is preferably close to zero as the ideal value. However, when the oxygen pumping by the main pump cell 21 is not excellently performed in the first inner space 20, the measurement gas flows out of the first inner space 20 toward the downstream side with oxygen is not sufficiently pumped out (with the set partial pressure is not achieved), and as a result, the value of the offset current becomes large. Thus, the value of the offset current can be regarded as an index indicating the degree of oxygen outflow from the first inner space 20, in other words, an index of the quality of oxygen pumping out of the first inner space 20 by the main pump cell 21.

Moreover, the oxygen concentration of 18% in the test gas is a relatively large value as compared to the oxygen concentration in an exhaust pipe of an engine, which is a use situation mainly assumed for the gas sensor 100. Thus, Determination 1 is intended for the oxygen pumping out from the first inner space 20 when the oxygen concentration in the measurement gas is high.

In the present example, the quality of the oxygen pumping out from the first inner space 20 was determined by applying the value of the offset current obtained by measurement to a determination index consisting of three levels of equal to or less than 0.1 µA, more than 0.1 µA and equal to or less than 0.3 µA, and more than 0.3 µA.

Specifically, for the gas sensor 100 having an offset current of 0.1 µA or less, it was determined that the oxygen pumping out from the first inner space 20 was performed enough by the main pump cell 21 so that the oxygen partial pressure in the first inner space 20 is controlled to a value set in advance.

For the gas sensor 100 having an offset current of more than 0.1 µA and 0.3 µA or less, the oxygen outflow from the first inner space 20 is slightly larger than in the above-described case, but the influence thereof on the NOx measurement accuracy is small, and thus it was determined that the measurement was possible.

For the gas sensor 100 having an offset current of more than 0.3 µA, oxygen flowed out from the first inner space 20 to the downstream side to the extent that it affects the measurement accuracy, which was determined to be not preferable.

(Determination 2)

Measurement (first measurement) using a test gas having an NOx concentration of 500 ppm and the balance of $N_2$ as a measurement gas, and measurement (second measurement) using a test gas having an oxygen concentration of 18%, an NOx concentration of 500 ppm, and the balance of $N_2$ as a measurement gas were performed with each gas sensor 100 manufactured as described above. The sensor element drive temperature was 830° C. The degree of NOx resolution in the first inner space 20 was determined based on the decrease rate (hereinafter referred to as Ip2 decrease rate) of the value of the NOx current Ip2 in the second measurement relative to the value of the NOx current Ip2 in the first measurement.

The small Ip2 decrease rate means that, even when a measurement gas having a high oxygen concentration is introduced into the first inner space 20, the influence therefrom on the NOx measurement accuracy is small. Thus, the Ip2 decrease rate can be regarded as an index having a correlation with NOx resolution in the first inner space 20, which occurs due to increase of the main pump voltage Vp0 upon introduction of the measurement gas having a high oxygen concentration into the first inner space 20.

In the present example, the quality of NOx resolution in the first inner space 20 was determined by applying the calculated value of the Ip2 decrease rate to a determination index consisting of three levels of equal to or less than 15%, more than 15% and equal to or less than 20%, and more than 20%.

Specifically, for the gas sensor 100 having an Ip2 decrease rate equal to or less than 15%, it was determined that the NOx resolution in the first inner space 20 was excellently suppressed.

For the gas sensor 100 having an Ip2 decrease rate more than 15% and equal to or less than 20%, the NOx resolution in the first inner space 20 occurred to some extent, but it was determined that the influence therefrom on the measurement accuracy was small.

For the gas sensor 100 having an Ip2 decrease rate more than 20%, the NOx resolution in the first inner space 20 had influence on the measurement accuracy, which was determined to be not preferable.

The Ip2 decrease rate threshold of 15% or 20% seems to be a high value at first glance. However, since the oxygen concentration of 18% in the test gas is a relatively large value as described above, setting of the threshold is appropriate.

(Result)

Table 1 lists the pre inner-space diffusion resistance, the space length L1, the space thickness t1, the length ratio L2/L1, the value of the width ratio w2/w1, and results of Determination 1 and Determination 2 for each gas sensor 100. Table 1 also lists the space width w1 and the electrode thickness sum $t2_{all}$. In Table 1, a double circle, a circle, or a cross is attached for each case in which the value of the offset current measured at Determination 1 is equal to or less than 0.1 µA, more than 0.1 µA and equal to or less than 0.3 µA, or more than 0.3 µA, respectively. In addition, a double circle, a circle, or a cross is attached for each case in which the value of the Ip2 decrease rate calculated in Determination 2 is equal to or less than 15%, more than 15% and equal to or less than 20%, or more than 20%, respectively.

TABLE 1

| No. | Pre inner-space diffusion resistance [$cm^{-1}$] | Space length L1 [mm] | Space thickness t1 [µm] | Electrode length L2/ Space length L1 | Electrode width w2/ space width W1 | Electrode thickness sum t2all [µm] | Space width w1 [µm] | Determination 1 | Determination 2 |
|---|---|---|---|---|---|---|---|---|---|
| 1 | 700 | 2.5 | 80 | 0.8 | 0.50 | 30 | 3.5 | ○ | ○ |
| 2 | 300 | 3.5 | 120 | 0.9 | 0.90 | 26 | 2.6 | ◎ | ◎ |
| 3 | 400 | 3.0 | 200 | 0.8 | 0.90 | 30 | 2.5 | ◎ | ◎ |
| 4 | 700 | 3.0 | 100 | 1.0 | 0.95 | 34 | 2.5 | ◎ | ◎ |
| 5 | 500 | 3.5 | 300 | 0.9 | 0.80 | 18 | 2.9 | ○ | ◎ |
| 6 | 600 | 3.0 | 50 | 0.9 | 0.50 | 10 | 2.0 | ○ | ○ |
| 7 | 200 | 3.0 | 80 | 0.7 | 0.75 | 30 | 3.1 | ○ | ○ |

TABLE 1-continued

| No. | Pre inner-space diffusion resistance [cm$^{-1}$] | Space length L1 [mm] | Space thickness t1 [μm] | Electrode length L2/ Space length L1 | Electrode width w2/ space width W1 | Electrode thickness sum t2all [μm] | Space width w1 [μm] | Determination 1 | Determination 2 |
|---|---|---|---|---|---|---|---|---|---|
| 8  | 800  | 2.5 | 100 | 0.5 | 0.60 | 60 | 1.5 | ○ | ○ |
| 9  | 1000 | 8.0 | 100 | 0.7 | 0.90 | 13 | 2.5 | ○ | ○ |
| 10 | 500  | 7.0 | 80  | 0.7 | 0.50 | 15 | 3.0 | ○ | ○ |
| 11 | 700  | 3.5 | 350 | 0.9 | 0.80 | 30 | 2.9 | X | ○ |
| 12 | 600  | 2.5 | 40  | 0.8 | 0.90 | 10 | 2.6 | ○ | X |
| 13 | 500  | 3.0 | 100 | 0.6 | 0.40 | 20 | 2.5 | ○ | X |
| 14 | 150  | 3.0 | 100 | 0.9 | 0.80 | 20 | 2.9 | ○ | X |
| 15 | 400  | 2.0 | 200 | 0.9 | 0.85 | 26 | 2.7 | X | X |
| 16 | 800  | 2.5 | 150 | 0.4 | 0.90 | 30 | 2.6 | X | X |

In Table 1, a double circle or a circle is attached for both of Determination 1 and Determination 2 only for the gas sensors 100 of No. 1 to No. 10 satisfying all requirements (a) to (d). This means that none of the oxygen outflow from the first inner space 20 toward the downstream side nor the NOx resolution in the first inner space 20, which affect the measurement accuracy of the NOx concentration, occurred only in these gas sensors 100. Meanwhile, a cross is attached for at least one of Determination 1 and Determination 2 for the gas sensors of No. 11 to No. 16 not satisfying at least one of the requirements (a) to (d).

The above results indicate that, with satisfying the requirements (a) to (d), a gas sensor 100 in which, even when a measurement gas having a high oxygen concentration is introduced into the first inner space 20, the influence of the introduction on the NOx measurement accuracy is small is achieved. Specifically, in the gas sensor 100, even when a measurement gas having a high oxygen concentration is introduced into the first inner space 20, the oxygen pumping out from the first inner space 20 is performed while the NOx resolution in the first inner space 20 is suppressed, at least in a range in which the NOx measurement accuracy can be ensured.

For the gas sensors 100 of No. 2 to No. 4, in particular, a double circle is attached for both of Determination 1 and Determination 2. This indicates that, in a gas sensor 100 satisfying the requirements (a) to (d) and additionally satisfying the following requirements (a') to (d'), even when a measurement gas having a high oxygen concentration is introduced into the first inner space 20, the oxygen partial pressure in the first inner space 20 is substantially maintained at a set value through the oxygen pumping out by the main pump cell 21 and the NOx resolution in the first inner space 20 does not occur and thus the NOx measurement accuracy hardly degrades.

(a') Space length L1: 3.0 mm or larger and 3.5 mm or smaller (b') Space thickness t1: 100 μm or larger and 200 μm or smaller (c') Length ratio L2/L1: 0.8 or more (1.0 or less)

(d') Width ratio w2/w1: 0.90 or more (1.0 or less)

While the invention has been shown and described in detail, the foregoing description is in all aspects illustrative and not restrictive. It is therefore understood that numerous modifications and variations can be devised without departing from the scope of the invention.

What is claimed is:

1. A gas sensor of a limiting current type, the gas sensor including a sensor element formed of an oxygen ion conductive solid electrolyte, the gas sensor being capable of specifying a concentration of NOx in a measurement gas, said sensor element includes:
  a gas inlet into which a measurement gas is introduced from an outer space;
  a first inner space communicated with said gas inlet under a predetermined diffusion resistance;
  a second inner space communicated with said first inner space under a predetermined diffusion resistance;
  a main pump cell which is an electrochemical pump cell constituted by an inner pump electrode including one or two unit electrode parts and provided to face said first inner space, an external pump electrode provided on a surface of said sensor element, and said solid electrolyte located between said inner pump electrode and said external pump electrode;
  a measurement electrode provided to face said second inner space and covered by a porous protection film providing a predetermined diffusion resistance, the measurement electrode functioning as a reduction catalyst for NOx;
  an atmospheric air introduction layer into which atmospheric air is introduced from outside of said sensor element as a reference gas;
  a reference electrode covered with said atmospheric air introduction layer; and
  a measurement pump cell which is an electrochemical pump cell constituted by said measurement electrode, said external pump electrode, and said solid electrolyte located between said measurement electrode and said external pump electrode, wherein when said inner pump electrode includes said two unit electrode parts, said two unit electrode parts are disposed to face each other, said main pump cell pumps out oxygen in said measurement gas introduced into said first inner space through an application of a predetermined main pump voltage between said inner pump electrode and said external pump electrode, so that oxygen partial pressure of said measurement gas in said first inner space is lowered, said measurement pump cell pumps out oxygen generated by a reduction of NOx in said measurement gas reaching near said measurement electrode in said measurement electrode, through an application of a predetermined pump voltage between said inner pump electrode and said external pump electrode, said gas sensor further includes:
  a controller which receives signals corresponding to a magnitude of an NOx current flowing between said measurement electrode and said external pump electrode in said measurement pump cell and specifies a concentration of said NOx based on the magnitude of the NOx current, a diffusion resistance from said gas inlet to said first inner space is 200 cm−1 or larger and 1000 cm−1 or smaller, and when said first inner space has a space length L1 as a size in a longitudinal direction of said sensor element, a space thickness t1 as a size in a thickness direction of said sensor element, and a space width w1 as a size in a width direction perpendicular to both of said longitudinal direction and said thickness direction, and said unit electrode part has an electrode length L2 as a size in said longitudinal direction and an electrode width w2 as a size in said width direction, said space length L1 is 2.5 mm or larger and 10 mm or smaller, said space thickness t1 is 50 μm or larger and 300 μm or smaller, a ratio of said electrode length relative to said space length is 0.5 or more and 1.0 or less, and a ratio of said electrode width relative to said space width is 0.5 or more 1.0 or less.

2. The gas sensor according to claim 1, wherein
said space length L1 is 3.0 mm or larger and 3.5 mm or smaller,
said space thickness t1 is 100 μm or larger and 200 μm or smaller,
the ratio of said electrode length relative to said space length is 0.8 or more and 1.0 or less, and
the ratio of said electrode width relative to said space width is 0.9 or more and 1.0 or less.

3. The gas sensor according to claim 2, wherein
in said one or two unit electrode parts,
an electrode thickness as a size in said thickness direction is 5 μm or larger and 30 μm or smaller,
an area is equal to or smaller than 20 mm2,
a total area of said inner pump electrode is equal to or larger than 10 mm2, and
a ratio of a sum of said electrode thickness relative to said space thickness is 0.06 or more and 0.60 or less.

4. The gas sensor according to claim 3, wherein
said sensor element further includes:
  a main-pump-control sensor cell which is an electrochemical sensor cell constituted by said inner pump electrode, said reference electrode, and said solid electrolyte located between said inner pump electrode and said reference electrode;
  an auxiliary pump cell which is an electrochemical pump cell constituted by an auxiliary pump electrode provided to face said second inner space, said external pump electrode, and said solid electrolyte located between said auxiliary pump electrode and said external pump electrode;
  an auxiliary-pump-control sensor cell which is an electrochemical sensor cell constituted by said auxiliary pump electrode, said reference electrode, and said solid electrolyte located between said auxiliary pump electrode and said reference electrode; and
  a measurement-pump-control sensor cell which is an electrochemical sensor cell constituted by said measurement electrode, said reference electrode, and said solid electrolyte located between said measurement electrode and said reference electrode,
said main pump cell pumps out oxygen in said measurement gas present in said first inner space through the application of said main pump voltage in accordance with an electromotive force generated between said inner pump electrode and said reference electrode in said main-pump-control sensor cell, between said inner pump electrode and said external pump electrode, said auxiliary pump cell pumps out oxygen in said measurement gas introduced into said second inner space through the application of the pump voltage in accordance with an electromotive force generated between said auxiliary pump electrode and said reference electrode in said auxiliary-pump-control sensor cell, between said auxiliary pump electrode and said external pump electrode, so that said measurement gas whose oxygen partial pressure has been further lowered compared to oxygen partial pressure in said first inner space reaches said measurement electrode, and said measurement pump cell pumps out oxygen generated in said measurement electrode through the application of the pump voltage in accordance with an electromotive force generated between said measurement electrode and said reference electrode in said measurement-pump-control sensor cell, between said measurement electrode and said external pump electrode.

5. The gas sensor according to claim 1, wherein
in said one or two unit electrode parts,
an electrode thickness as a size in said thickness direction is 5 μm or larger and 30 μm or smaller,
an area is equal to or smaller than 20 mm2,
a total area of said inner pump electrode is equal to or larger than 10 mm2, and
a ratio of a sum of said electrode thickness relative to said space thickness is 0.06 or more and 0.60 or less.

6. The gas sensor according to claim 2, wherein
said sensor element further includes:
  a main-pump-control sensor cell which is an electrochemical sensor cell constituted by said inner pump electrode, said reference electrode, and said solid electrolyte located between said inner pump electrode and said reference electrode;
  an auxiliary pump cell which is an electrochemical pump cell constituted by an auxiliary pump electrode provided to face said second inner space, said external pump electrode, and said solid electrolyte located between said auxiliary pump electrode and said external pump electrode;
  an auxiliary-pump-control sensor cell which is an electrochemical sensor cell constituted by said auxiliary pump electrode, said reference electrode, and said solid electrolyte located between said auxiliary pump electrode and said reference electrode; and
  a measurement-pump-control sensor cell which is an electrochemical sensor cell constituted by said measurement electrode, said reference electrode, and said solid electrolyte located between said measurement electrode and said reference electrode,
said main pump cell pumps out oxygen in said measurement gas present in said first inner space through the application of said main pump voltage in accordance with an electromotive force generated between said inner pump electrode and said reference electrode in said main-pump-control sensor cell, between said inner pump electrode and said external pump electrode, said auxiliary pump cell pumps out oxygen in said measurement gas introduced into said second inner space through the application of the pump voltage in accordance with an electromotive force generated between said auxiliary pump electrode and said reference electrode in said auxiliary-pump-control sensor cell, between said auxiliary pump electrode and said external pump electrode, so that said measurement gas whose oxygen partial pressure has been further lowered compared to oxygen partial pressure in said first inner space reaches said measurement electrode, and said measurement pump cell pumps out oxygen generated in said measurement electrode through the application of the pump voltage in accordance with an electromotive force generated between said measurement electrode and said reference electrode in said measurement-pump-control sensor cell, between said measurement electrode and said external pump electrode.

7. The gas sensor according to claim 5, wherein
said sensor element further includes:
- a main-pump-control sensor cell which is an electrochemical sensor cell constituted by said inner pump electrode, said reference electrode, and said solid electrolyte located between said inner pump electrode and said reference electrode;
- an auxiliary pump cell which is an electrochemical pump cell constituted by an auxiliary pump electrode provided to face said second inner space, said external pump electrode, and said solid electrolyte located between said auxiliary pump electrode and said external pump electrode;
- an auxiliary-pump-control sensor cell which is an electrochemical sensor cell constituted by said auxiliary pump electrode, said reference electrode, and said solid electrolyte located between said auxiliary pump electrode and said reference electrode; and
- a measurement-pump-control sensor cell which is an electrochemical sensor cell constituted by said measurement electrode, said reference electrode, and said solid electrolyte located between said measurement electrode and said reference electrode, said main pump cell pumps out oxygen in said measurement gas present in said first inner space through the application of said main pump voltage in accordance with an electromotive force generated between said inner pump electrode and said reference electrode in said main-pump-control sensor cell, between said inner pump electrode and said external pump electrode, said auxiliary pump cell pumps out oxygen in said measurement gas introduced into said second inner space through the application of the pump voltage in accordance with an electromotive force generated between said auxiliary pump electrode and said reference electrode in said auxiliary-pump-control sensor cell, between said auxiliary pump electrode and said external pump electrode, so that said measurement gas whose oxygen partial pressure has been further lowered compared to oxygen partial pressure in said first inner space reaches said measurement electrode, and said measurement pump cell pumps out oxygen generated in said measurement electrode through the application of the pump voltage in accordance with an electromotive force generated between said measurement electrode and said reference electrode in said measurement-pump-control sensor cell, between said measurement electrode and said external pump electrode.

8. The gas sensor according to claim 1, wherein
said sensor element further includes:
- a main-pump-control sensor cell which is an electrochemical sensor cell constituted by said inner pump electrode, said reference electrode, and said solid electrolyte located between said inner pump electrode and said reference electrode;
- an auxiliary pump cell which is an electrochemical pump cell constituted by an auxiliary pump electrode provided to face said second inner space, said external pump electrode, and said solid electrolyte located between said auxiliary pump electrode and said external pump electrode;
- an auxiliary-pump-control sensor cell which is an electrochemical sensor cell constituted by said auxiliary pump electrode, said reference electrode, and said solid electrolyte located between said auxiliary pump electrode and said reference electrode; and
- a measurement-pump-control sensor cell which is an electrochemical sensor cell constituted by said measurement electrode, said reference electrode, and said solid electrolyte located between said measurement electrode and said reference electrode, said main pump cell pumps out oxygen in said measurement gas present in said first inner space through the application of said main pump voltage in accordance with an electromotive force generated between said inner pump electrode and said reference electrode in said main-pump-control sensor cell, between said inner pump electrode and said external pump electrode, said auxiliary pump cell pumps out oxygen in said measurement gas introduced into said second inner space through the application of a pump voltage in accordance with an electromotive force generated between said auxiliary pump electrode and said reference electrode in said auxiliary-pump-control sensor cell, between said auxiliary pump electrode and said external pump electrode, so that said measurement gas whose oxygen partial pressure has been further lowered compared to oxygen partial pressure in said first inner space reaches said measurement electrode, and said measurement pump cell pumps out oxygen generated in said measurement electrode through the application of the pump voltage in accordance with an electromotive force generated between said measurement electrode and said reference electrode in said measurement-pump-control sensor cell, between said measurement electrode and said external pump electrode.

* * * * *